United States Patent
Fercher (10) Patent No.: US 11,317,799 B2
(45) Date of Patent: May 3, 2022

(54) OPHTHALMOLOGICAL LENGTH MEASUREMENT BY MEANS OF DUAL-BEAM SPACE-TIME DOMAIN WAVELENGTH TUNING LOW-COHERENCE INTERFEROMETRY

(71) Applicant: Carl Zeiss Meditec AG, Jena (DE)

(72) Inventor: Adolf Friedrich Fercher, Weissensee (AT)

(73) Assignee: Carl Zeiss Meditec AG, Jena (DE)

( * ) Notice: Subject to any disclaimer, the term of this patent is extended or adjusted under 35 U.S.C. 154(b) by 497 days.

(21) Appl. No.: 16/097,609

(22) PCT Filed: May 2, 2017

(86) PCT No.: PCT/EP2017/060410
§ 371 (c)(1),
(2) Date: Oct. 29, 2018

(87) PCT Pub. No.: WO2017/191128
PCT Pub. Date: Nov. 9, 2017

(65) Prior Publication Data
US 2020/0323429 A1    Oct. 15, 2020

(30) Foreign Application Priority Data

May 3, 2016 (AT) .................. A 226/2016

(51) Int. Cl.
*A61B 3/00*     (2006.01)
*G02B 27/10*    (2006.01)
(Continued)

(52) U.S. Cl.
CPC ............ *A61B 3/111* (2013.01); *A61B 3/0091* (2013.01); *A61B 3/1005* (2013.01); *G02B 27/106* (2013.01)

(58) Field of Classification Search
CPC ....... A61B 3/111; A61B 3/0091; A61B 3/102; A61B 3/1005; A61B 3/12–125;
(Continued)

(56) References Cited

U.S. PATENT DOCUMENTS 5,684,562 A * 11/1997 Fujieda .................. A61B 3/107
                                                        351/211
7,695,140 B2 * 4/2010 Fercher .................. A61B 3/102
                                                        351/221
(Continued)

FOREIGN PATENT DOCUMENTS

AT         511 740 B1     2/2013
AT         518602 A1     11/2017
(Continued)

OTHER PUBLICATIONS

PCT International Search Report and Written Opinion for International Application No. PCT/EP2017/060410, dated Aug. 9, 2017, 15 pages.
(Continued)

*Primary Examiner* — Travis S Fissel
(74) *Attorney, Agent, or Firm* — Patterson Thuente Pedersen, P.A.

(57) ABSTRACT

Measurement of intraocular lengths by dual-beam Fourier low-coherence interferometry on the basis of Fresnel-zone-type space-time domain interferograms of the Purkinje-Sanson reflexes. The eye is illuminated by parallel, monochromatic dual beams having wavelengths which differ in temporal sequence. Wavelength spectra of space-time domain interferograms are imaged onto a photodetector array and registered. Viewing direction and position of the eye are fixed by optical aids and are monitored by acoustic and optical aids. A zoom optical unit in the output beam of the ophthalmological interferometer makes it possible, by simple focusing, to image virtual Fresnel-zone-type space-
(Continued)

time domain interferograms from contrast-optimized positions onto the photodetector array or onto an image intensifier that is arranged in front of the photodetector array such that the position-dependent size change of the space-time domain interferograms is compensated by the scale change of this imaging.

11 Claims, 4 Drawing Sheets

(51) Int. Cl.
  *A61B 3/10* (2006.01)
  *A61B 3/11* (2006.01)
(58) Field of Classification Search
  CPC .. G01B 9/02; G01B 9/02009; G01B 9/02063;
    G01B 9/0209; G01B 9/02091
  USPC ................................ 351/205–221, 237, 239
  See application file for complete search history.

(56) References Cited

U.S. PATENT DOCUMENTS

| | | | | |
|---|---|---|---|---|
| 2007/0076217 A1* | 4/2007 | Baker | .................... | A61B 3/102 356/498 |
| 2008/0013960 A1* | 1/2008 | Tearney | ............. | G02B 21/0048 398/139 |
| 2009/0033870 A1* | 2/2009 | Hangai | .................. | A61B 3/024 351/206 |
| 2011/0102802 A1* | 5/2011 | Izatt | ....................... | A61B 3/102 356/479 |
| 2012/0281185 A1* | 11/2012 | Juhasz | ................... | A61B 3/152 351/208 |
| 2013/0242259 A1* | 9/2013 | Hacker | .................. | A61B 3/102 351/206 |
| 2015/0168125 A1* | 6/2015 | Arieli | ................. | G01B 9/02036 351/211 |
| 2017/0241908 A1* | 8/2017 | Feke | ......................... | G01J 1/58 |

FOREIGN PATENT DOCUMENTS

| | | |
|---|---|---|
| DE | 103 23 920 A1 | 12/2004 |
| DE | 10 2011 011 277 A1 | 8/2012 |
| EP | 1 946 039 B1 | 7/2008 |
| WO | WO 2007/053971 A1 | 5/2007 |

OTHER PUBLICATIONS

English translation of International Search Report for International Application No. PCT/EP2017/060410, dated Aug. 9, 2017, 6 pages.
English translation of Written Opinion of the ISA for International Application No. PCT/EP2017/060410, dated Aug. 9, 2017, 3 pages.
Hrebesh Molly Subhash et al: "Full-Field and Single-Shot Full-Field Optical Coherence Tomography: A Novel Technique for Biomedical Imaging Applications", Advances in Optical Technologies, vol. 1315, No. 3, Jan. 1, 2012 (Jan. 1, 2012), pp. 205-226, XP055150097, ISSN: 1687-6393, DOI: 10.1155/2012/435408.
Fercher et al., "Measurement of intraocular distances by backscattering spectral interferometry", Opt. Commun. 117(1995)43-48.
Seelamantula et al., Éxact and efficient signal reconstruction in frequency-domain optical-coherence tomography J. Opt. Soc. Am A, 25(2008)1762-1771).
English translation of International Report on Patentability for PCT International Search Report and Written Opinion for International Application No. PCT/EP2017/060410, dated May 2, 2017, 9 pages.

* cited by examiner

OPHTHALMOLOGICAL LENGTH MEASUREMENT BY MEANS OF DUAL-BEAM SPACE-TIME DOMAIN WAVELENGTH TUNING LOW-COHERENCE INTERFEROMETRY

RELATED APPLICATIONS

This application is a National Phase entry of PCT Application No. PCT/EP2017/060410 filed May 2, 2017, which application claims the benefit of priority to AT Application No. A 226/2016, filed May 3, 2016, the entire disclosures of which are incorporated herein by reference.

FIELD OF THE INVENTION

Ophthalmological partial-distance length measurement is used in the ophthalmology to dimension removal parameters for the refractive surgery and to dimension lens implants for the refractive surgery and for the cataract surgery.

BACKGROUND

Low-Coherence Interferometrical Length Measurement in the Ophthalmology

Ophthalmological Interferometry:

The calculation of the refractive power of the lens that is to be implanted for the cataract surgery or the calculation of the adjusting of the refractive power for the refractive surgery is carried out by use of various biometric formulas based on pre-surgical eye parameters such as eye length, cornea thickness, corneal curvature, anterior chamber depth, refractive power of the lens and lens thickness. To accomplish this, the optical low-coherence interferometry (LCI) is used nowadays, since it—in contrast to the previously used acoustic measurement—works without any contact and because it is more precise by at least 1 dimension. Corresponding measuring devices are offered commercially by e.g. the companies Carl Zeiss Meditec AG, Haag-Streit AG and NIDEK Co. and are described in e.g. the patents DE 103 23 920 A1 (Zeiss) and EP 1 946 039 B1 (Haag-Streit).

Figure 1A:
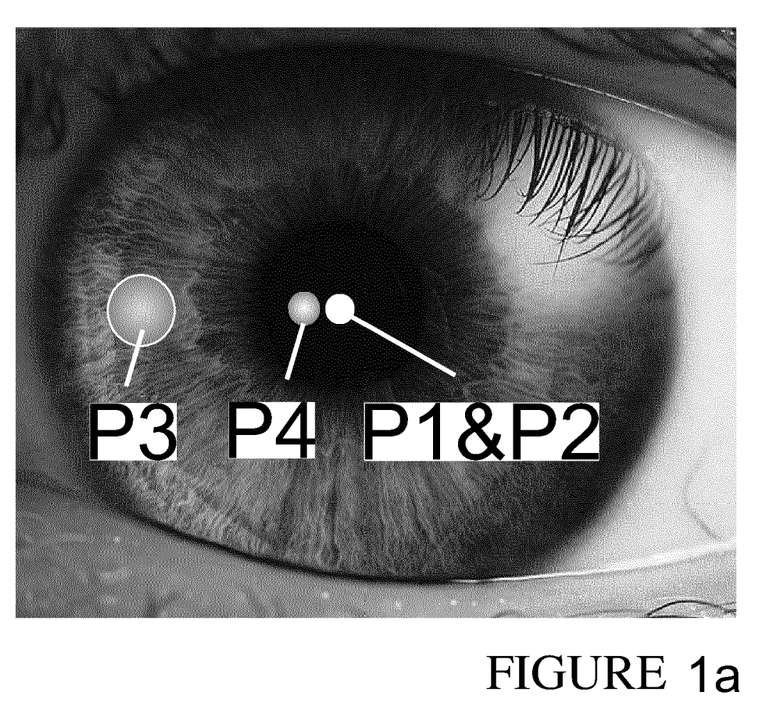
FIG. 1a: Purkinje-Sanson images P1, P2, P3, P4.

Ophthalmological Interferogram:

If an eye is illuminated from the front sideways, it is known to be possible to see the Purkinje-Sanson images P1, P2, P3 and P4 somewhat separated from one another, as it is depicted in FIG. 1a. These are images of the light source illuminating the eye, created by a reflection at the ophthalmic optics interfaces.

P1 is formed by a reflection on the cornea front surface, P2 by a reflection at the corneal inner surface, P3 by a reflection at the lens front surface, and P4 by a reflection at the lens rear surface. Along with the light that is reflected by the ocular fundus, the reflexes that correspond to the Purkinje-Sanson images form the basis for the LCI interferometry at the eye.

Figure 1B:
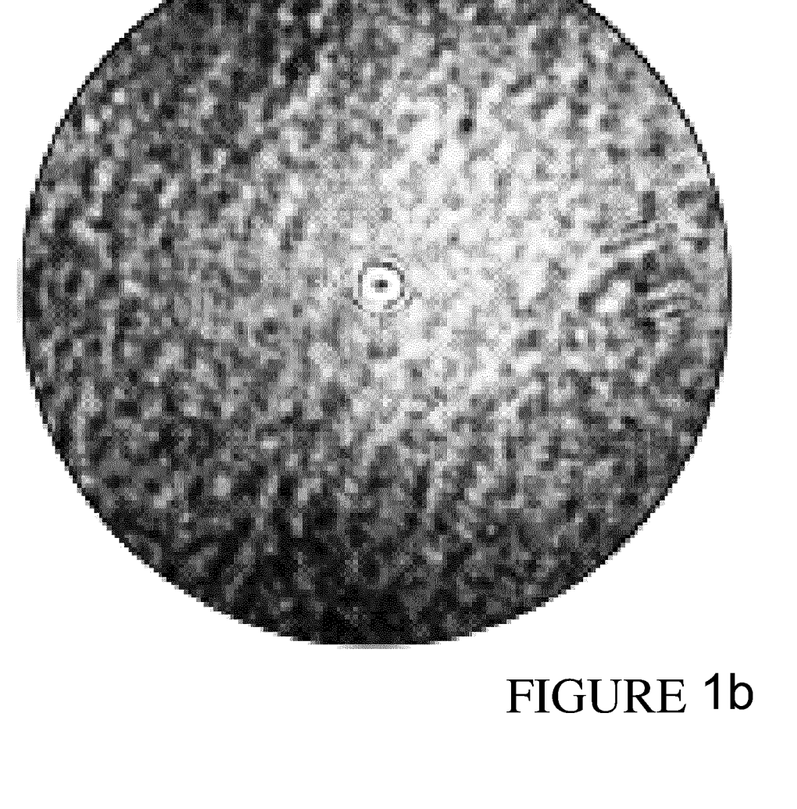
FIG. 1b: Fresnel-zone like space-time domain interferogram (RZI) embedded in the center of the speckle structure in front of the eye.
Figure 1C:
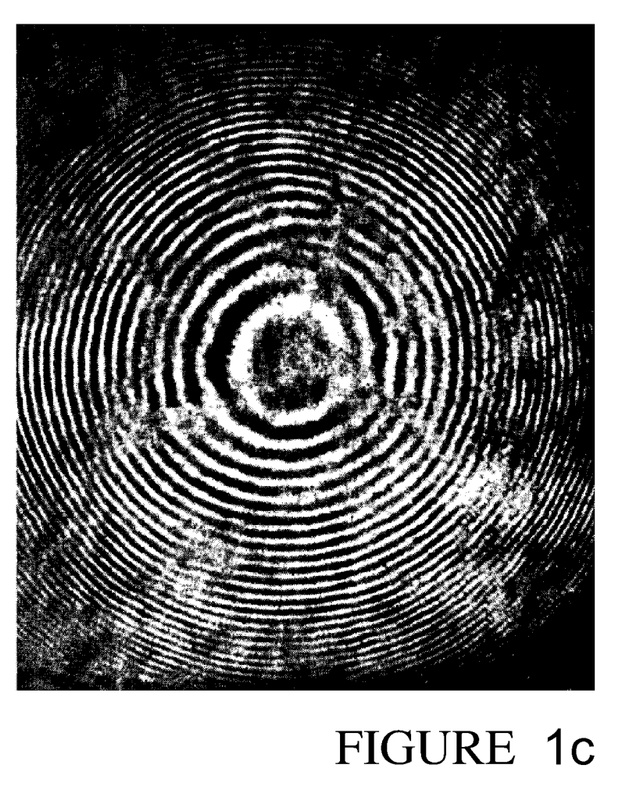
FIG. 1c: Enlarged section of the RZI from FIG. 1b and
FIG. 2: Beam path in an arrangement according to an example embodiment of the invention.

If the eye is illuminated by temporally coherent light, a speckle field can be observed in the space in front of the eye and interferences of the light rays of the Purkinje-Sanson reflexes that are embedded in this space-time domain: FIG. 1b shows a snapshot of this Fresnel zone-like space-time domain interferogram (RZI) embedded in the speckle structure; FIG. 1c shows an enlarged section thereof. This figure is the space-domain interferogram of the fundus reflex and the corneal reflex. Due to the pulse-synchronous change in the size of the globe, the local phase in this interferogram temporally changes, the interference rings pulsate synchronously in radial direction with the cardiac pulse, hence: "space-time domain interferogram". Individual rays of this RZI form the rays of the LCI interferometry.

The RZI depicted in FIG. 1c is the most distinctive one among several similar RZI's that were generated by the various Purkinje-Sanson reflexes. It is caused by interference between the wave reflected at the corneal anterior surface and the one reflected from the fundus. The RZI is a cross-section through a 3-dimensional interference phenomenon of the 2 mentioned waves, which consist of concentric, alternatingly light (constructive interference) and dark (destructive interference) interference hollow cones, that appear with increasing diameter along the optical axis of the eye.

Partially congruent—when there is a regular anatomy of the eye—RZI also appear between the fundus reflex and the reflexes from the inner surface of the cornea as well as the front surface of the eye lens.

The AT 511 740 B1 describes a solution in this regard that is based on a complete space-time domain low-coherence interferogram. The interferometric alignment by application of both, the visual or digital image pattern recognition, or otherwise based on image pairs of the eye that are illuminated from the front is hereby carried out by application of oppositely-phased space-time domain low-coherence interferograms. To register the space-time domain interferograms, a two-dimensional detector array is used.

Dual-Beam LCI-Interferometry:

If temporally low-coherent light is used, the interference phenomena between the Purkinje-Sanson reflexes and the reflex of the fundus disappear. However, if the eye is illuminated with a dual-beam made up of two low-coherent light beams within one interferometer, which are internally temporally offset from each other, it is possible to make the respective RZI visible again, provided that the path difference ΔL of these 2 light beams matches—within the coherence length $l_c$—the optical length of the distance of the corresponding interfaces in the eye. The same applies to the interferences of the LCI interferometry, which are pointedly based on individual rays.

Such a method is described in the US 2015/0168125 A1. In this case a "fringe pattern" is generated from within the interferometer, which is to be imaged into a particular object-layer of the eye that is to be measured, such as the retina, the lens, or the tear film on the cornea. A broadband, tunable light source is used in this case. The described solution offers the possibility to measure the eye 2-dimensionally without scanning.

This path difference ΔL=c·Δt, which can easily be measured in the interferometer, with c=speed of light and Δt=time difference of the dual beam components, provides the basis for both, the LCI interferometry as well as the WT-interferometry that is used in this application. The determining value for the resolution capacity of this measuring method is the coherence length.

$$l_c = 2 \cdot \ln 2 \cdot l_0^2/(\pi \cdot \Delta \lambda) \qquad (1)$$

with an average wavelength $\lambda_0$ and the FWHM (full width at half maximum) bandwidth Δλ, of the light rays—assuming the use of one of the most commonly used light sources, such as super light-emitting diodes, well illuminated Gaussian spectra. This is the dual-beam time domain LCI measuring method; it is based on the adaption of easily measurable interferometer-internal path differences at an optical path difference in the eye and is thus not dependent on movements of the eye as a whole in relation to the measuring device. It provides —without any other provisions—the structure of the eye at x=y=0, i.e. on the visual axis along the measuring beam.

Fresnel-zone-like space-time domain interferograms (RZI's) can be observed as real interferograms in front of the eye (in FIG. 2 at z>0) as well as virtual interferograms in and behind the eye (in FIG. 2 at z<0) and can not only be used selectively at certain points, but also on the entire surface, for the LCI interferometry at the eye. Due to the unusual anatomy of the eye when compared to other organs (dominating of regular reflexes as opposed to otherwise dominating diffuse reflection), it is possible to also use localized interferences for the measuring of the lengths in the eye—at a normal anatomy—in the z-positions outside of the eye, and to transfer its off-axial x-y-position correspondingly; such RZI's in front of the eyes form the basis for the patent application described here.

As an alternative to the above-mentioned dual-beam LCI interferometry, it is also possible to illuminate the eye with a single low-coherence light ray and to divide the object light that come back from the eye by means of a dual-beam interferometer into 2 light rays that are offset in illumination direction by a path length difference $\Delta L$, which only produce an interferogram, if the path difference $\Delta L$ of these 2 light rays—within the coherence length of $l_c$—corresponds to the optical length of the distance of two boundary surfaces in the eye.

Wavelength tuning interferometry (WT interferometry): One disadvantage of the above-mentioned dual-beam time-domain LCI interferometry is the necessary tuning of the path difference $\Delta L$ in the interferometer, as well as the fact that the current measuring signal or interferogram is only based on light portions with the corresponding $\Delta L$, the rest generates noise. In contrast to this, the Fourier LCI interferometry uses all the light reflected from the object. In the WT interferometry variant of the Fourier LCI technology (also referred to as "Swept-Source" or "Swept Wavelength Laser" LCI interferometry), the ophthalmological interferometer is illuminated in chronological order by a sequence of monochromatic light rays. The thereby gained spectrum of the light reflections from the interferometer is the Fourier transform of the amount of scattering potential of the object or the object structure along the measuring beam, see equation (2) in section 4D-b.

Cataract:

The cataract is defined as optical inhomogeneity of the lens of the eye. It hereby refers to opacities and refraction inhomogeneities. So-called water vacuoles (liquid-filled vacuoles or gaps) can be observed at the age-related cataract. The Cataracta nuclearis (nuclear cataract) leads to a brownish opacity and an increase in refractive power. A frequent occurrence are mixed types of these morphological cataract forms. There is no therapy by use of medication. Cataract surgery is nowadays the most commonly performed ophthalmic surgery in the Western Hemisphere. In the cataract surgery (e.g. in Germany about 400,000 per year), the natural eye lens is replaced by an artificial intraocular lens, for example by one that is made of Plexiglas.

LCI interferometry for cataract: Compared to the ultrasound techniques that were used in the past, the ocular distance measurement by application of optical dual-beam LCI interferometry eliminates erroneous measurements under favorable conditions and quickly leads to the result in normal anatomy. However, current LCI technologies are not sufficiently sensitive e.g. for denser cataracts. In this regard there is a gap in the provision of medical care, which, however, mainly affects patients in developing countries.

The Fourier LCI interferometry as well as the use of longer wavelengths, solves this problem only to a certain extent.

The sensitivity of LCI interferometry is primarily determined by the power of the measuring beam at the test object. An increased sensitivity would be possible as such—due to power density of the illumination beam in the pupil, which is limited by safety regulations—by using the entire cross-section of the beam of the light that is reflected from the eye when the pupil is opened at its maximum. However, this is not automatically possible because of the phase of the space domain interferogram which is variable via the cross-section of the beam. The recently proposed solution for this problem by the applicant by means of the more sensitive space-time domain interferometry (AT 511 740 81) does provide a correspondingly high sensitivity due to the greater energy flow within the measuring beam, but it requires a complex image processing.

Furthermore, there is a problem in that many cataracts are inhomogeneous, due to which the measuring beam diameter and the measuring beam position have to be arranged in a flexible manner. Even with patients that seem to show no apparent irregularities, a certain degree of variance of the eye parameters has to be expected, which requires the greatest possible flexibility in the illumination of the eye and for the registration of the RZI.

SUMMARY OF THE INVENTION

The invention therefore provides methods and arrangements for the ophthalmological length measurement that allow that the position and diameter of the measuring beam within the pupil of the eye that is to be measured can be arranged freely and that offers short measuring times and a usability even for denser cataracts due to a high sensitivity. The invention will be explained with reference to the FIGS. 1 and 2 with the therein used reference numbers.

Figure 2:
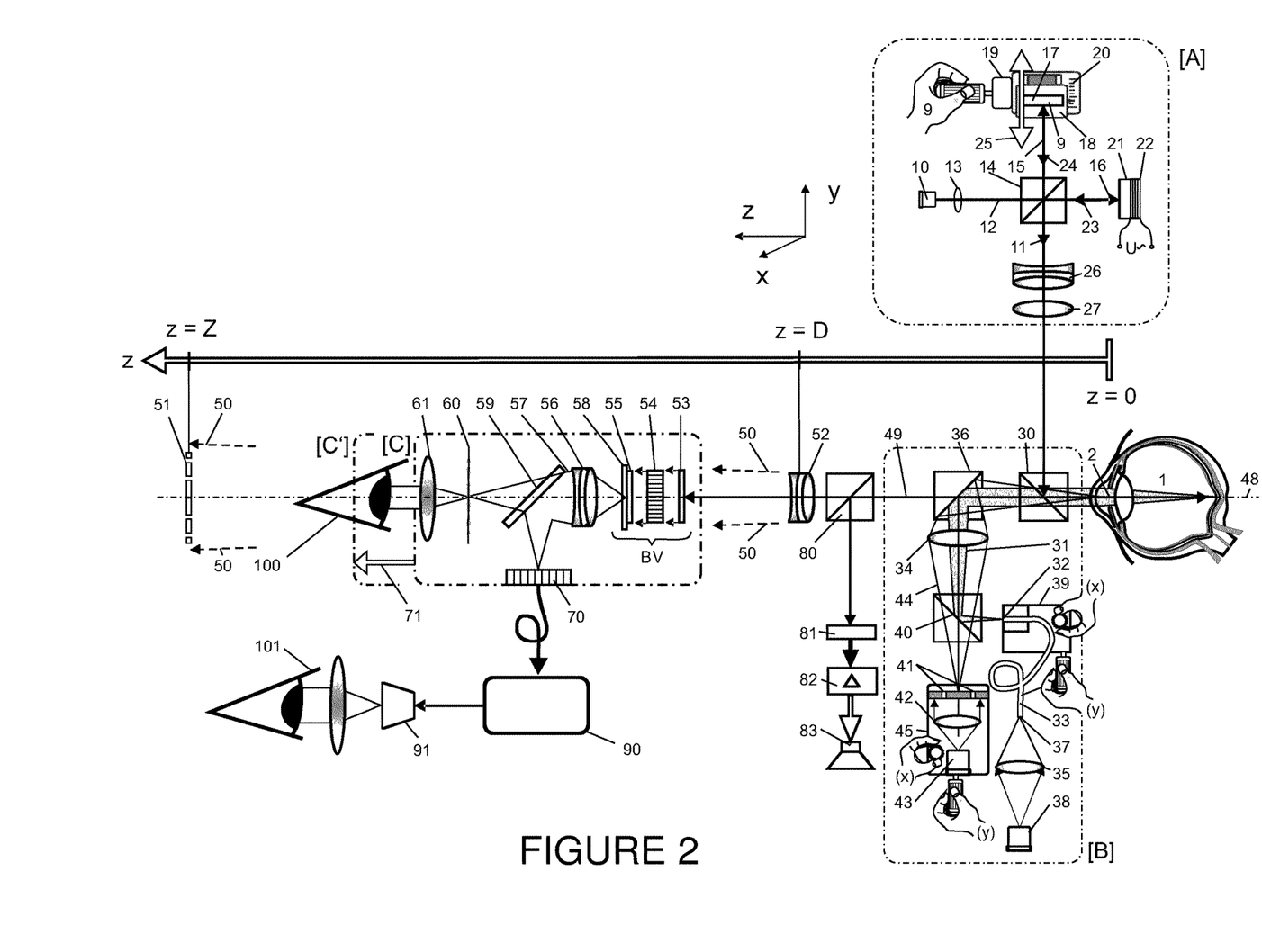

The technical objective on which the invention is based on is achieved by application dual-beam space-time domain WT interferometry in that the test person's eye 1 is illuminated in chronological order in correspondence with the dual-beam LCI of one wavelength spectrum of monochromatic measuring dual-beams made up of two mutually temporally offset coaxial components and the structure of the eye is calculated from the spectrum of the intensity data $I_{(\xi,\Psi)}(k)$ from the scattered field that was scattered and/or reflected by the eye, wherein the stray field intensity data $I_{(\xi,\Psi)}(k)$ that is required for calculating the structure of the eye is obtained from transverse $\xi$-$\Psi$ positions of real Fresnel zone-like space-time domain interferograms RZI's 51 that are a few cm to dm distant in longitudinal direction from the eye at z=Z by means imaging these onto a photodetector array 70, whose photodetector signal data is passed on to a computer 90, wherein a zoom lens 52 is arranged in the output beam 49 of the ophthalmological interferometer (box [A]) which is optically coupled to the eye in such a way for the mentioned imaging, that it, functioning as an inverse magnifying glass, makes it possible via its focal length setting along the visual axis 48 of the eye with the RZI 51, being positioned with different contrast for the stripes, to image it with maximum contrast onto an image intensifier photocathode 53 that is firmly positioned in z-direction or onto such a photodetector array 70, and which is further positioned within the output beam 49 of the interferometer on its axis in such a way that the increase in the ring diameter of the RZI that is occurring along the visual axis of the eye in z-direction is compensated on the photodetector array 70 or on the image intensifier photocathode 53 due to the scale of the image of the RZI that is decreasing with increasing distance from the eye (1) in z-direction, wherein the monochromatic dual-beams of different wavelengths 11, that are illuminating the interferometer, are generated by a tunable laser 10 and by a beam splitter 14 in a Michelson interferometer; furthermore, that the eye 1 is illuminated by two fixation beams 31, 44 of different color that are coaxial with the measuring dual-beams in order to facilitate the adjustment of the eye, one beam of which, fixing the direction of the eye, is generated by imaging the output surface 32 of a light-guiding optical fiber 33 through an optics 34 onto the fundus of the eye, and the other beam, serving for the positioning of the eye, is generated by imaging a circular ring-shaped illuminated aperture 41 on the sclera or on the environment of the pupil 2 of the eye 1 and further, for controlling the state of the interferometer, one of the partial beams of the measuring dual-beam 11 within the Michelson interferometer that is generating the dual-beam is reflected by a retroreflector 21 which periodically moves back and forth in small increments, e.g. by $\lambda/4$, with a sound frequency f, so that a portion of the output beam 49, that is directed towards a photodetector 81 with amplifier 82 and speaker 83, signaled by means of signal tones in the frequency f, that the light from the ophthalmological interferometer has reached the BV via the eye. The space-time domain technology hereby provides a high flexibility of the measurement on the one hand by accessing I×J intra-ocular distances that are running parallel towards each other within segments of the eye pupil that can arbitrarily be adapted and positioned larger and in a flexible way, and thus for base points of the wave surface in these areas and therefore also for the transfer function of the optics of the eye as well as, alternatively, by forming summations and averages of the intra-ocular paths lengths within any pupil segments a substantial increase in the sensitivity.

DETAILED DESCRIPTION

The invention is hereby explained in more detail on the basis of an example embodiment according to FIG. 2.

In the beam path of an arrangement according to the invention as it is shown in FIG. 2, the ophthalmological interferometer in the narrower sense [A], the fixation light components [B] and the device for checking and detecting of the measuring signal [C] are delimited by dash-dotted lines for clarity.

4A. Ophthalmological Interferometer:

The measuring method described here uses interferometers in an unconventional way in that the eye is not illuminated by a single measuring beam, but rather by a measuring dual-beam generated by a Michelson interferometer. The Michelson interferometer in the narrower sense comprises the components 10 to 27. 9 is the hand of the observer (medical assistant) that is carrying out the measuring of the length. 10 is the light source for the measuring dual-beam 11. The measuring light source 10 is a spatially coherent light source (DSL) that can be tuned in its wavelength, e.g. a tunable, spatially coherent laser. The light beam 10 that is emitted by the measuring light source 12 is collimated by the optics 13 and divided by the beam splitter 14 into two partial beams 15 and 16.

The partial beam 15 is reflected by the measuring mirror 17 that can be moved parallel to the beam direction (y-direction) as a partial beam 24 of the measuring dual-beam 11 towards the beam splitter 30. The retroreflector 17 is mounted on a moveable table 18 which is adjustable in a controlled manner by the hand 9 or by means of an electric drive 19 and its y-position can be read out by use of a built-in position sensor or it can be read by use of a nonius 20 by an observer. Similar to the space-domain dual-beam LCI interferometry technology, a path difference $\Delta L$ that is intrinsic to the dual-beam 11 is also set in relation to the partial beam 16 in this case. This path difference plays an important role in tackling the auto correlation problem that was mentioned in section 4D-a.

The partial beam 16 impinges on a retroreflector 21, which is mounted on a piezoelectric actuator 22 and, powered by an AC voltage "U~", it periodically moves back and forth in the beam direction (z-direction) in small increments, e.g. by $\lambda/4$, with an audio frequency f. As a result, the herein reflected partial beam 23 of the measuring dual-beam 11 experiences a temporally periodic phase shift with reference to the partial beam 24. This serves for the monitoring of the adjustment by use of an audio signal; it is interrupted upon initiation of the measurement or at the start of the signal registration by the photodetector signal. Both reflected partial beams 23 and 24 are finally reflected or transmitted by the beam splitter 14 as a measuring dual-beam 11 in the direction of the beam splitter 30 and are reflected by the latter onto the eye (1).

The beam expander consisting of zoom-ocular 26 and lens 27 serves for the adjusting of the measuring beam diameter to the size of the pupil. The zoom-ocular 2 in FIG. 26 is not shown by the drawn combination of a converging lens and a diverging lens in its actual structure, but only symbolically. (The same applies to the zoom optics 52 and 56)

4B. Beam Parameters and Fixation of the Test Person's Eye:

The basic parameters of the measurement beam in the pupil of the test person are the beam intensity, the beam diameter and the wavelength as well as the beam direction and beam position in relation to the direction and position of the visual axis of the eye. Beam intensity: The admissible limit value for the radiation strength (radiation power with reference to the beam cross-section area) of the light rays that reach the eye is limited by safety regulations and depends, in addition to the wavelength, on the radiation duration that is to be expected.

Beam Diameter:

On the one hand, it determines the overall radiation power that is entering into the eye and thus the achievable sensitivity of the length measurement. On the other hand, the beam diameter limits the illumination of the pupil and thus e.g. the maximum expansion of the measurable transfer function of the eye.

Wavelength:

The herein dominating Rayleigh-Scattering increases by $1/\lambda^4$. The use of light with a greater wavelength is therefore advantageous, but it is increasingly restricted by the absorption in the tissue water starting at approx. $\lambda=1.4$. (currently DSL's in the wavelength range of approximately 680 nm up to ~3 µm are commercially available)

Beam Direction with Reference to the Visual Axis:

It is defined by the direction of the fixing light beam 31, wherein the test person looks at the light spot that was generated by the fixing light beam on his retina. The fixing light beam 31 is generated by an image of the output surface 32 of the light conductor 33 through optics 34 and the optics of the patient's eye 1 via the beam splitters 40, 36 and 30 on his fundus. The optical fiber 33 is illuminated by a light-emitting diode (LED) 38, which emits e.g. green light, whose light is bundled by an optics 35 onto the input surface 37 of the optical fiber 33. The x-y position of the output surface 32 of the optical fiber 33 determines the direction of the fixing light beam 31; it is positioned by use of a 2-coordinate adjusting device 39 in 2 directions that are orthogonal towards each other, e.g. in x- and y-direction.

Measuring Position with Reference to the Visual Axis:

This is controlled by use of a light ring that is projected onto the patient's eye. To generate this light ring, a circular ring-shaped aperture 41 is reflected by use of a fixing light beam 44 through the optics 34, reflected by the beam splitter 36, and through the beam splitter 30 onto the sclera or onto the environment of the pupil 2 of the patient's eye 1. The aperture opening 41 is illuminated with the aid of a lens 42 by use of LED 43 which emits e.g. red light. In this way the patient can have an active part in the positioning. The position of the eye 1 is adjusted by operation of a 2-coordinate adjusting device 45 in 2 directions that are orthogonal to each other, e.g. in x- and y-direction. As a criterion for the standard position of the patient's eye, it is possible to use the symmetrical brightness perception of the patient for the respective wavelength or color of the light emitted by the LED 43.

4C. Position Monitoring and Registration of the RZI:

A monitoring of the positioning of the input pupil 2 of the patient's eye in relation to the light ring image is made possible by use of an image of the pupil layer via the zoom optics 52 at the interferometer output via the image intensifier (BV) in the focal plane 60 of the ocular 61. To accomplish this, the focal length and/or z-position (the origin of z is located in the center point of the curvature of the cornea, about 8 mm away from the cornea vertex on the inner side of the anterior chamber of the eye) of the zoom optics 52 are set in such a way, that the pupil 2 is imaged onto the photocathode of 53 of the BV.

Such a BV can be based e.g. on a micro channel plate technology, made up of photocathode 53 at the input, micro channel plate 54 for amplification in the narrower sense and phosphor screen 55 at the output of the BV. The spectral sensitivity of this BV is determined by the respective photo cathode material. However, beyond a wavelength of 1 μm, the detectivity of the herein available solid-state photo receiver decreases by $1/\lambda^2$. As an alternative, it is also possible to use a digital camera, based on CCD technology, electron multiplying CCD or intensified CCD technology instead of such a BV. In the latter cases, the sensor of the digital camera replaces the photocathode, the phosphor screen 55 is replaced by the electronic viewfinder.

Visual Monitoring of the Position:

The reinforced RZI occurring at the phosphor screen 55 of the BV simplifies the finding of the RZI by the observer 100 (with the help of the microscope-analogous optics 56 and 61) or by the observer 101 (by imaging onto the array 70 and transfer by computer 90 onto monitor 91), in particular when there is an irregular optics of the eye. There is furthermore a reticle 58 as an aid for the visual monitoring of the present RZI position in the layer of the phosphor screen 55 of the BV. The observation of the image at the output of the BV on the reticle that is arranged on it makes it easier to position and align the eye of the test person. (The latter can be further adjusted by use of the fixing light beam 31)

Alignment Monitoring Via Audio Signal:

A more general checking of the adjustment status of the ophthalmological interferometer is supported by use of an acoustic observation. For this purpose, a beam splitter 80 is located within the output beam 49 of the ophthalmological interferometer, which directs a portion of the output beam onto a photodetector 81 comprising an amplifier 82 and a speaker 83. A sound with the frequency f that occurs at the actuator 22 when the AC voltage U~ is switched on, indicates that light from the ophthalmological interferometer reaches the BV via the eye.

By varying of the focal length of the zoom optics 52, the contrast of an RZI 51 that is imaged on the BV is first of all optimized for the interferometric measuring, the RZI is then imaged onto the photodetector array 70 by means of the portion of the image beam 57 that is reflected by the beam splitter 59 and it is then measured or "scanned" by its photodetector grid.

Fresnel-Zone-Like Interferograms RZI 51:

The light beam bundle 50, which is reflected by the eye, in this case characterized by the "output beam" 49 of the ophthalmological interferometer, contains a series of 3-dimensional interference phenomena in form of interference hollow cones with increasing diameter along the optical axis of the eye. In the case of a regular anatomy of the eye, all these interferograms superimpose, wherein the interferogram of the strong reflexes of the fundus and of the two corneal reflexes dominate. On the other hand, the corneal reflexes and the reflex of the rear lens surface feature almost the same curvature radius and therefore almost the same interference state across the entire pupil of the eye, so that the (monochromatic) interferograms that are formed by these when they are illuminated with light of a higher coherence length can hardly be recognized as being separate when visually inspected. In the case of an irregular anatomy, e.g. in the case of a cataract, it could be possible under certain circumstances that no complete or only speckle-like interferograms can be observed.

The interesting high-contrast RZI's are primarily present as real interferences in the area in front of the cornea ($z>0$) and as virtual interferences behind the cornea ($z<0$). Real high-contrast interferences are localized on the z-axis (several cm to dm) in front of the eye. For the zoom optics 52 that is arranged in front of the eye, these are virtual objects and they are imaged by it—by way of a reverse-operating magnifying glass—as real images onto the BV-input or onto a photodetector array that is positioned there.

These interferograms form the basis for the ophthalmologic WT-interferometry variant of the LCI length measurement. It is thus basically possible to measure a series of intraocular distances in each point of the pupil (x, y). In the case of a regular anatomy of the eye, due to the dominating of the regular reflexes for the RZI, there is a definite allocation of the interferogram positions for the corresponding x-y-positions in the EP of the eye. In this way access to e.g. the distribution of the optical length of eye cornea/fundus or of the eye's anterior chamber depth cornea/lens of the eye within the pupil is gained. In each case, it is possible to add the measured lengths across the entire pupil and to thus obtain a signal with a very high sensitivity—however, due to the sum of different lengths, these are obtained at the price of a reduced accuracy.

Incidentally, the RZI 51 that is used for the measurement is located—when observed by the test person—behind the zoom optics 52 (at $z>D$). Thus, the distance of the RZI that is used for the measuring of the zoom optics does not have any influence of enlarging the interferometer in z-direction.

The zoom optics 52 can also be directly adjacent to beam splitter 80 or, when the adjusting aids are omitted, to beam splitter 36.

4D. Signal Processing.

4D-a. Intensity Spectra of the Light Waves that are Emitting from the Eye:

The herein used WT-interferometry or Swept-Source LCI interferometry—there are several techniques that are based on the same optical principles but with different and yet synonymous names—is based on the intensity spectrum $I_{\xi\Psi}(k)$ of the light waves that are emitting from the eye at the transversal object position $(\xi,\Psi)$. These are generated by use of spectrally tunable lasers as light source, they are then forwarded by a detector to a computer 90 where they provide via Fourier transformation and auto correlation decoding the object structure in the transversal object position $(\xi,\Psi)$ along the measuring beam in the ophthalmological interferometer [A].

In an example method according to the invention, the scattered-field intensity spectrum $l_{x,y}(k)$ of the patient's eye that is required for the calculation of the subsurface structure of the eye is registered by a photodetector array (70) from transversal positions of an RZI (51) which is localized in longitudinal z-direction some cm to dm outside the patient's eye, and is then transferred to a computer (90). Due to the regular reflexes that are also dominating at these distances even in moderate cataracts, a definite allocation of the RZI positions to the transverse pupillary coordinates is largely provided.

4D-b. Fourier Transformation of the RZI Array Data:

The computer 90 saves the spectrum of the ocular scattered-field intensity data $I_{x,y}(k)$ of the individual array photodetectors, calculates from these the transversal positions (x, y) of the lengths data of the partial sections corresponding to the array photodetectors and displays these on the connected monitor 91.

The array data refers to data matrices $l_{x,y}(k)$ with $$l_{x,y}(k) \sim |FT_z\{F_{x,y}(z)\}|^2 \quad (2)$$

wherein $FT_z$=Fourier transformation with reference to the z-coordinate; $k=2\pi/\lambda$ is the wave number, $\lambda$ the wavelength of the light beam that is emitted from the DSL. $l_{x,y}(k)$ refers to the spectral intensity data that is allocated to the individual array photodetectors and registered by light propagation outside of the patient's eye's pupil (via the optics 52 and 56 as well as the BV). The DSL 10 is hereby tuned by a spectrum $\Delta\lambda$, the size of which determines the depth resolution, see equation (1).

$$F_{x,y}(z) \sim n^2(x,y,z) - 1$$

is the scattering potential of the eye or its "structure", n(x,y; z) is the corresponding refractive index.

The signal strength of the used light that is hereby scattered back is high at locations with adjacent tissues with great scattering potential differences. Therefore, the z-positions of tissue boundaries $z_{Gi/Gj}(x, y)$ along each respective light beam in the eye pupil position (x, y) can be determined by use of the signal intensity peaks that are occurring there (the index Gi/Gj refers to "tissue boundary between tissue Gi and tissue Gj" with e.g.: G1/G2=cornea anterior surface/corneal interior surface, G1/G3=corneal anterior surface/lens anterior surface, G4/G5=lens interior surface/fundus). The corresponding lengths of the partial sections are obtained as the difference $\Delta z_{Gi/GJ}$ of the z-values of these signal intensity peaks along the beams through the pupil position (x, y).

The following variants can hereby be used: (a) The use of the measured lengths of the partial sections $\Delta z_{Gi/Gj}$ in the pupil for the determination of the optometric data or the transfer function of the patient's eye. (b) The use of the measurable partial amounts of the lengths of the partial sections $\Delta z_{Gi/Gj}(x,y)$ with segments of the pupil, in particular in the case of an advanced cataract. (c) The forming of average values of the measurable lengths of the partial sections $\Delta z_{Gi/Gj}(x,y)$ across several or all points of the pupil for an increase of the sensitivity.

Resolution and Measurement Range:

The transversal resolution, by use of which the RZI is registered, is provided in accordance with the classic Abbe resolution formula by use of the wavelength and numeric aperture of the image through the optics 52. The depth resolution is provided by a tuning of the DSL 10 via a spectrum coherence length of the imaging light beam.

However, the size of the measuring range is determined by the density of the sample values on the k-axis.

Auto Correlation:

However, an inverse FT of the intensity data of the photodetector array 70 does not—automatically—provide the object structure, but rather its auto correlation function. To solve this problem, there are a number of techniques, which are described in detail in the literature (e.g. Fercher et al., Opt. Commun. 117 (1995) 43-48 or Seelamantula et al., J. Opt. Soc. Am A, 25 (2008) 1762-1771) and which can also be used in this case.

4D-c. Size and Contrast of the RZI; Role of the Sampling Theorems:

Both, the position D and the focal length of the zoom optics 52 determine the imaging scale of the RZI that is projected onto the photocathode 53 of the BV and further onto the array 70—or onto a photodetector array 70 that is localized without the interposition of a BV. Generally, the size of the RZI at the photodetector array via zoom optics 56 is of course to be selected in such a way, that it is "sampled" by the array detectors in the correct distance—in accordance with the sampling theorem. The central interferogram circular surface of an RZI and furthermore also its ring structure up to the 4. interference ring—in accordance with the sampling theorem—can be sampled by means of e.g. a 32×32 photo detector array. In contrast to a mere detection of the central interferogram circular surface, this leads to a sensitivity gain of already 6 dB for the sum signal (when disregarding the Gaussian profile and with a homogeneous transparency of the eye media, the size of the sum signal of the photodetector-array increases with the surface of the registered RZI). A photodetector array comprising 1000× 1000 pixel furthermore features a sensitivity potential in the range of 20 dB when used in accordance with the sampling theorem.

4D-d. RZI Size and Sensitivity:

However, an optimal RZI contrast is given in individually different z-positions (within a few cm to dm in front of the patient's eye). If different z-positions of the RZI 51 (via the optics of 52 and 56 and the BV) are imaged onto the detector array 70 to optimize the contrast, this is done due to the necessary tuning of the focal length of the zoom optics 52 via individually different imaging scales in dependence of parameters of the eyes. The sampling of the image of the RZI 51, which is varying in its size, onto photodetector array 70 thus often leads to an "undersampling" or "oversampling", due to which the image quality and sensitivity is impaired.

Homogenization of the Size of the RZI.

2 steps are thus necessary for the signal optimizing.

1. The locating of an RZI with an optimal contrast along the z-axis.
2. An image of the RZI from the phosphor screen 55 of the BV by the zoom optics 56 onto the photodetector array 70 which is in accordance with the sampling theorem.

This is a 2-dimensional diversity of possibilities and is therefore not practicable.

Since the ring diameter of the RZI, which is caused by the increase in the curvature radii of the corneal reflexes that are expanding, increase with growing distance z from the patient's eye, whereas the imaging scale of the RZI on the photocathode of the BV reduces with increasing distance from the optics 52, it is possible to compensate the size variation of the RZI along the z-axis by a suitable selection of the RZI imaging scale—or by a suitable selection of the position and/or focal length of the zoom optics 52. As an example, a positioning of the zoom optics 52 at z=D=60 mm in front of eye 1 is assumed. In this way it is possible to achieve—by means of a corresponding zoom-optics 52 focal length—a consistency of the RZI ring diameter that is imaged on the photocathode 53 by more than +/−5% for the z-positions between z=100 mm-600 mm.

Alternatively, it is possible to move the apparatus for the detection of the measuring signal [C] along the z-axis instead of a tuning of the focal length of the zoom optics 52 (e.g. towards position C', see open arrow 71).

4D-e. Strongly Inhomogeneous Transparency of the Patient's Eye's Media:

In such cases, an advantage of the method according to the invention is, that the detector array, which is possibly much larger in comparison to the single detector, provides a considerable relief with regard to the otherwise standard point-for-point spectral interferometry comprising only one single tiny detector which requires a much more laborious signal search and also a segmentation of histologically interrelated areas.

The invention claimed is:

1. An arrangement for ophthalmological length measurement by dual-beam space-time domain wavelength tuning interferometry, comprising
   a double-beam interferometer that illuminates a patient's eye with a measuring dual-beam;
   a tunable laser that illuminates the double-beam interferometer and thus generates a tunable measuring dual-beam made up of paired monochromatic, temporally offset coaxial components at an output of the interferometer, which illuminates the patient's eye after being reflected at a beam splitter; and
   wherein the structure of the eye is calculated from a spectrum of scattered-field intensity data $I_{\xi,\Psi}(k)$ of a scattered and/or reflected scattered-field that is emitted from the patient's eye;
   wherein the scattered-field intensity data $I_{\xi,\Psi}(k)$ that is necessary for calculation of structure of the eye is imaged onto an image intensifier or a photodetector array via a lens from the space-time domain interferogram (RZI) of an output beam of the patient's eye localized in transversal $\xi$-$\Psi$-positions in longitudinal direction in front or behind the cornea, and are then transferred to a computer; and
   optics designed as a zoom lens arranged within the output beam of the interferometer, wherein the zoom lens functions as an inverse magnifying glass and images differently positioned space-time domain interferograms in z-direction via a focal length setting thereof along the visual axis of the eye onto a fixed position of the image intensifier or of the photodetector array in z-direction thereby imaging the space-time domain interferograms of the eye from contrast-optimized positions onto the photodetector array.

2. The arrangement for the ophthalmological length measurement by dual-beam space-time domain wavelength tuning interferometry according to claim 1, wherein the scattered-field intensity data $I_{\xi,\Psi}(k)$ that is necessary for calculation of structure of the eye is imaged onto the image intensifier and wherein the image intensifier comprises a photocathode at an input thereof, a microchannel plate that amplifies the image and a phosphor screen at an output thereof.

3. The arrangement for the ophthalmological length measurement by dual-beam space-time domain wavelength tuning interferometry according to claim 1, wherein the space-time domain interferograms are positioned on the image intensifier or wherein the optics, which is imaging the photodetector array, is positioned within the output beam on the z-axis such that an increase of a ring diameter of a Fresnel zone-like space-time domain interferograms along the visual axis of the eye is compensated by a scale of the image of the RZI on the photodetector array or on the image intensifier, which is decreasing in z-direction with increasing distance from the eye.

4. The arrangement for the ophthalmological length measurement by dual-beam space-time domain wavelength tuning interferometry according to claim 1, wherein the monochromatic dual-beams of different wavelengths are generated by the tunable laser and a second beam splitter in a Michelson interferometer.

5. The arrangement for the ophthalmological length measurement by dual-beam space-time domain wavelength tuning interferometry according to claim 1, further comprising two fixation light beams that illuminate the patient's eye wherein the two fixation light beams are coaxial with regards to the measuring dual-beams and feature different colors for direction of the patient's eye.

6. The arrangement for the ophthalmological length measurement by dual-beam space-time domain wavelength tuning interferometry according to claim 5, wherein the fixation light beams for the direction of the patient's eye are implemented by an imaging of an guiding light conductor output surface of a light-guiding light conductor through a lens onto a fundus of the eye.

7. The arrangement for the ophthalmological length measurement by dual-beam space-time domain wavelength tuning interferometry according to claim 5, wherein the fixation light beams for the direction of the patient's eye are implemented by a light ring that is projected on the patient's eye by imaging an aperture that is illuminated in a circular ring-shaped manner onto the sclera or onto the area of the pupil of the patient's eye.

8. The arrangement for the ophthalmological length measurement by dual-beam space-time domain wavelength tuning interferometry according to claim 1, wherein one of the partial beams of the measuring dual-beam is reflected in the Michelson Interferometer, which generates the dual-beam, by utilization of a retro-reflector, which moves back and forth periodically.

9. The arrangement for the ophthalmological length measurement by dual-beam space-time domain wavelength tuning interferometry according to claim 8, wherein the retroreflector moves back and forth by a distance of $\lambda/4$, at an audio frequency, wherein $\lambda$, is an average wavelength of the paired monochromatic beams.

10. The arrangement for the ophthalmological length measurement by dual-beam space-time domain wavelength tuning interferometry according to claim 1, further comprising a second beam splitter that is arranged within the output beam of the ophthalmological interferometer and that directs a portion of the output beam onto the photodetector comprising an amplifier and a speaker.

11. The arrangement for the ophthalmological length measurement by dual-beam space-time domain wavelength tuning interferometry according to claim 1, wherein measurements of intraocular distances are possible at each point of the pupil (x, y).

* * * * *

UNITED STATES PATENT AND TRADEMARK OFFICE
CERTIFICATE OF CORRECTION

PATENT NO. : 11,317,799 B2
APPLICATION NO. : 16/097609
DATED : May 3, 2022
INVENTOR(S) : Fercher It is certified that error appears in the above-identified patent and that said Letters Patent is hereby corrected as shown below:

On the Title Page

On Page 2, in Item (56), under "Other Publications", in Column 2, Line 12, delete "Éxact" and insert -- Exact --

On Page 2, in Item (56), under "Other Publications", in Column 2, Line 14, delete "25(2008)1762-1771)." and insert -- 25(2008)1762-1771. --

In the Specification

Column 5, Line 39, delete "P4" and insert -- P4; --

Column 5, Line 43, delete "FIG. 1b and" and insert -- FIG. 1b; and --

Column 6, Line 39, delete "56)" and insert -- 56.) --

Column 6, Line 64, delete "available)" and insert -- available.) --

Column 7, Line 67, delete "31)" and insert -- 31.) --

Column 9, Lines 51-52, delete "n(x,y; z)" and insert -- n(x,y,z) --

In the Claims

Column 11, Line 40, in Claim 1, delete "comprising" and insert -- comprising: --

Column 12, Line 64, in Claim 9, delete "wherein λ," and insert -- wherein λ --

Signed and Sealed this
Fourteenth Day of October, 2025

John A. Squires
*Director of the United States Patent and Trademark Office*